United States Patent
Schoenlein

(10) Patent No.: US 9,377,391 B2
(45) Date of Patent: Jun. 28, 2016

(54) LIGHT OR WEATHERING TESTING DEVICE COMPRISING A SPECIMEN ENCLOSURE WITH AN INTEGRATED UV RADIATION FILTER

(71) Applicant: Artur Schoenlein, Ruesselsheim (DE)

(72) Inventor: Artur Schoenlein, Ruesselsheim (DE)

(73) Assignee: Artur Schoenlein, Ruesselsheim (DE)

( * ) Notice: Subject to any disclaimer, the term of this patent is extended or adjusted under 35 U.S.C. 154(b) by 0 days.

(21) Appl. No.: 14/470,338

(22) Filed: Aug. 27, 2014

(65) Prior Publication Data

US 2015/0041678 A1    Feb. 12, 2015

Related U.S. Application Data

(63) Continuation of application No. 12/015,845, filed on Jan. 17, 2008, now abandoned.

(30) Foreign Application Priority Data

Jan. 17, 2007    (DE) .......................... 10 2007 002 415

(51) Int. Cl.
  *G01N 17/00*   (2006.01)
  *G01N 17/02*   (2006.01)
  *B01J 19/12*   (2006.01)

(52) U.S. Cl.
  CPC ............. *G01N 17/004* (2013.01); *B01J 19/123* (2013.01); *G01N 17/002* (2013.01)

(58) Field of Classification Search
  CPC .............................. G01N 17/00; G01N 17/004
  See application file for complete search history.

(56) References Cited

U.S. PATENT DOCUMENTS

| 1,827,530 | A | * | 10/1931 | Le Grand | ......................... 600/21 |
|---|---|---|---|---|---|
| 2,523,322 | A | * | 9/1950 | Ornstein | ............... G01N 17/00 236/44 R |
| 3,433,949 | A | * | 3/1969 | Truhan | ................. G01N 17/004 250/455.11 |
| 3,500,682 | A | * | 3/1970 | Newfield | .................... 73/150 R |
| 3,664,188 | A | * | 5/1972 | Kockott | ..................... 73/150 R |
| 3,675,477 | A | * | 7/1972 | Allen | .......................... 73/150 R |
| 3,686,940 | A | * | 8/1972 | Kockott | ..................... 73/150 R |
| 3,693,020 | A | * | 9/1972 | Ackerman, Jr. | ............... 250/372 |
| 3,983,742 | A |   | 10/1976 | Suga | |
| 4,012,954 | A | * | 3/1977 | Klippert | .............. G01N 17/004 73/150 R |
| 4,154,925 | A | * | 5/1979 | Hlavka | ........................ 536/13.1 |
| 4,391,522 | A |   | 7/1983 | Schmid et al. | |
| 4,544,995 | A | * | 10/1985 | Suga | ............................. 362/225 |
| 4,627,287 | A |   | 12/1986 | Suga | |
| 4,698,507 | A | * | 10/1987 | Tator et al. | .................... 250/429 |

(Continued)

FOREIGN PATENT DOCUMENTS

DE           43 30 756           3/1995
EP         1157744 A1    *    11/2001

(Continued)

OTHER PUBLICATIONS

Search Report for European Patent Application No. 08 000 112.6, Apr. 29, 2010. 5 pages.

*Primary Examiner* — Michael Logie
(74) *Attorney, Agent, or Firm* — Vedder Price PC

(57) ABSTRACT

The device comprises a chamber in which a UV radiation source and an enclosure are arranged, the enclosure comprising a bottom wall for mounting a specimen, a UV radiation filter facing the bottom wall and a plurality of sidewalls interconnecting the bottom wall and the UV radiation filter.

5 Claims, 4 Drawing Sheets

(56) References Cited

U.S. PATENT DOCUMENTS

| | | | |
|---|---|---|---|
| 4,731,255 A | 3/1988 | Maeda et al. | |
| 4,747,645 A * | 5/1988 | Rudzki | 356/51 |
| 4,770,542 A | 9/1988 | Takagi et al. | |
| 4,817,447 A * | 4/1989 | Kashima et al. | 73/865.6 |
| 4,880,988 A | 11/1989 | Witt | |
| 4,931,655 A | 6/1990 | Yoshida et al. | |
| 4,995,273 A * | 2/1991 | Kisima et al. | 73/865.6 |
| 5,206,518 A * | 4/1993 | Fedor et al. | 250/504 R |
| 5,220,840 A * | 6/1993 | Neigoff et al. | 73/865.6 |
| 5,459,322 A * | 10/1995 | Warkentin | 250/455.11 |
| 5,476,636 A | 12/1995 | Tomiita et al. | |
| 5,660,794 A | 8/1997 | Gilbreath et al. | |
| 5,898,816 A | 4/1999 | Heeger et al. | |
| 6,285,137 B1 * | 9/2001 | Grossman et al. | 315/291 |
| 6,537,419 B1 | 3/2003 | Kinnard | |
| 6,646,278 B1 | 11/2003 | Schwarz et al. | |
| 6,649,921 B1 | 11/2003 | Cekic et al. | |
| 6,872,936 B2 * | 3/2005 | Rathod et al. | 850/63 |
| 6,984,058 B2 * | 1/2006 | Morris et al. | 362/253 |
| 6,990,868 B2 * | 1/2006 | Hardcastle, III | G01N 3/60 374/5 |
| 7,013,742 B2 | 3/2006 | Beraud | |
| 7,025,831 B1 | 4/2006 | Butterbaugh et al. | |
| 7,174,781 B2 * | 2/2007 | Webb | G01N 17/004 73/170.16 |
| 7,214,412 B2 | 5/2007 | Nishiguchi et al. | |
| 7,368,730 B2 | 5/2008 | Schonlein et al. | |
| 7,485,883 B2 | 2/2009 | Gardner, III | |
| 7,544,948 B2 * | 6/2009 | Schonlein et al. | 250/372 |
| 8,156,830 B2 * | 4/2012 | Kaji et al. | 73/865.8 |
| 8,653,484 B2 * | 2/2014 | Rudolph et al. | 250/492.1 |
| 2002/0187070 A1 * | 12/2002 | Mori et al. | 422/53 |
| 2003/0150560 A1 * | 8/2003 | Kinnard | C23C 16/45504 156/345.33 |
| 2004/0065852 A1 * | 4/2004 | Harrell et al. | 250/504 R |
| 2004/0093965 A1 * | 5/2004 | Hardcastle, III | 73/865.6 |
| 2004/0231440 A1 | 11/2004 | Bearaud | |
| 2005/0120811 A1 * | 6/2005 | Hardcastle, III | 73/865.6 |
| 2006/0139931 A1 * | 6/2006 | March et al. | 362/293 |
| 2006/0268401 A1 | 11/2006 | Fischer et al. | |
| 2007/0298362 A1 | 12/2007 | Rocha-Alvarez et al. | |
| 2008/0169428 A1 * | 7/2008 | Schoenlein | 250/453.11 |
| 2013/0287966 A1 * | 10/2013 | Sleiman et al. | 427/558 |
| 2013/0306883 A1 * | 11/2013 | Lim | 250/492.1 |

FOREIGN PATENT DOCUMENTS

| | | |
|---|---|---|
| GB | 1 320 355 | 6/1973 |
| JP | 57000544 | 1/1982 |
| JP | 64-66542 | 3/1989 |
| JP | 05072116 | 3/1993 |
| JP | 09061295 | 3/1997 |

* cited by examiner

Fig. 2

LIGHT OR WEATHERING TESTING DEVICE COMPRISING A SPECIMEN ENCLOSURE WITH AN INTEGRATED UV RADIATION FILTER

CROSS-REFERENCE TO RELATED APPLICATIONS

This application is a continuation of U.S. patent application Ser. No. 12/015,845, filed Jan. 17, 2008, which claims priority to German Application No. 10 2007 002 415.2, filed Jan. 17, 2007, both of which are wholly incorporated herein by reference.

FIELD OF THE INVENTION

The present invention relates to a light or weathering testing device and to an enclosure for one such device.

BACKGROUND OF THE INVENTION

The object of devices for artificial weathering material specimens is to estimate the useful life of materials which in application are continually exposed to natural weather conditions and thus degrade under climatic influencing factors such as light and heat of the sun, moisture, and the like. To obtain a good simulation of the natural weather conditions the spectral energy distribution of the light generated in the device needs to correspond as best possible to that of natural sunlight, this being the reason why xenon radiators are employed as the source of radiation in such devices. Accelerated aging testing materials is achieved by irradiating the specimens constantly and with added intensity to speed up aging of the specimens.

The majority of the material specimens tested in artificial weathering devices are made of plastics in which the degradation due to exposure to the weather is mainly caused by the UV component of sunlight. The photochemical primary processes involved, i.e., photon absorption and the generation of energized conditions or free radicals proceed independently of temperature, whereas the subsequent steps in the reaction may be temperature-dependent as a function of the polymers or additives involved and thus the aging of the materials as observed is likewise temperature-dependent.

The aforementioned devices for artificial weathering of specimens comprise as a rule, in addition to the source of radiation, further means with which other artificial weather conditions such as, for example, high humidity, rain or noxious emissions can be generated. In addition to these artificial weathering devices light testing devices also find application which simply contain a source of radiation. Such light testing devices can be used, for example, to determine the sun protection factor or light protection factor of chemical or physical light protection factors such as UV light protection factors. For determining the sun protection factor the spectral energy distribution of the sun is defined from 290 nm to 400 nm. Defined as the standard sun is, e.g., spectral distribution as specified in DIN 67501, whereby the spectral radiation intensity extends down to $10^{-5}/10^{-6}/W/m^2$. In sun simulators as used in weathering tests such requirements do not exist. The spectral energy distribution of the sun as specified in CIE 85 (Table 4) begins not before 305 nm and is assumed to be 0 at 300 nm, whereby the spectral radiation intensity is of the order of 0.1 $W/m^2$ and higher.

In weathering devices known hitherto usually one or more UV radiation sources such as xenon radiators are made use of. These are appreciated to provide a good simulation of the solar spectrum. But, the emitted radiation comprises relatively high spectral properties in the infrared and UV spectral range which need to be suitable filtered. As regards the UV component, the xenon radiator can be filtered with a WG320 filter of corresponding thickness in thus satisfying the aforementioned requirements on a standard sun for determining the sun protection factor.

Conventional weathering apparatuses have, however, the following drawbacks. Usual xenon radiators having a doped quartz crystal envelope emit radiation with wavelengths up to 250 nm. A commercially available WG320 filter (made by Schott) cannot be bent, this being the reason why strips 10 mm wide and 300 mm long need to be placed together. The radiation can pass at the locations where the filters come together or where metal blanks contact each other. In addition to this, changes in temperature can displace the filter edge. The edge location of the WG320 filter depends on the ambient temperature of the filter (temperature drift 0.06 nm/K). The tolerances on the testing requirements for determining the light protection factor by the COLIPA method are so tight that a change in ambient temperature of 40° K can result in the test being out of tolerance. Since the filters are furthermore arranged in the vicinity of the xenon radiator the ambient temperature for the filters is between 70° C. and 110° C. depending on the output of the lamp. This means that the WG320 filters need to be between 0.7 to 1 mm thick, resulting in the assembly as a whole being highly unstable with strips 10 mm wide and approximately 300 mm long.

SUMMARY OF THE INVENTION

The present invention is thus based on the object of defining a device for light or weathering testing specimens with which the UV radiation of a UV radiation source can now be filtered reliably defined.

This object is achieved by the features of claim 1. Advantageous further embodiments and aspects are recited in the sub-claims and the further independent claims.

The gist of the present invention is providing the UV radiation filter as part of an enclosure enveloping the specimen at least in part.

The device for light or weathering testing a specimen in accordance with the invention comprises a chamber, an UV radiation source sited in the chamber and an enclosure arranged in the chamber including an enclosure wall comprising a UV radiation filter, the enclosure enveloping the specimen at least in part.

One substantial advantage of the device in accordance with the invention is that the UV radiation filter is no longer sited in the direct vicinity of the xenon radiator. This now does away with all means needed in conventional devices for mounting the UV radiation filter in the vicinity of the xenon radiator. Instead, the UV radiation filter is now configured as part of the enclosure or enclosure wall and thus mounted like the enclosure, it no longer being necessary to adjoin a plurality of strips of filters to surround the xenon radiator. Instead, providing an enclosure now makes it possible to close it off light-tight inwards so that no stray radiation whatsoever from the xenon radiator gains access to the specimen. In other words, now, only the UV radiation emitted by the xenon radiator directly reaches the specimen from the xenon radiator. When the UV radiation filter is sited as part of the enclosure so that it is disposed between the xenon radiator and the specimen, only filtered UV radiation can gain access to the specimen in thus reliably avoiding the specimen being impinged by stray radiation.

Another advantage of the present invention is that the UV radiation filter is no longer exposed to high thermal stress because it is no longer located in the direct vicinity of the xenon radiator. Since some distance away from the xenon radiator, because of the temperature control, no such fluctuations in temperature occur as in the vicinity of the xenon radiator, the transmission characteristic of the UV radiation filter can now be maintained constant, it being particularly when using an edge filter such as a WG320 filter that the edge length can be maintained constant due to the temperature being relatively stable. This now makes it possible, for example, to satisfy the tolerances specified for determining the light protection factor in accordance with pertinent standards, for example DIN 67501 or the COLIPA method. A further advantage of the device in accordance with the invention is that due to the fact that the UV radiation filter is no longer in the direct vicinity of the xenon radiator, there is now greater freedom in designing the UV radiation filter, particularly the thickness of the UV radiation filter.

In one preferred embodiment of the device in accordance with the invention it is provided for that the enclosure comprises a bottom wall for mounting the specimen, an UV radiation filter sited facing the bottom wall and a plurality of sidewalls interconnecting the bottom wall and the UV radiation filter. In this arrangement it may be provided for in particular that the top wall facing the bottom wall of the enclosure is formed entirely by the UV radiation filter. It is, however, just as possible that the UV radiation filter is formed by a window within the top wall.

The UV radiation filter has preferably the shape of a rectangular disk, the enclosure comprising four sidewalls each of which joins a side edge of the UV radiation filter to the bottom wall to make it possible to configure the enclosure light-tight so that no stray light whatsoever or substantially no stray light of the xenon radiator attains the specimen. In this arrangement the light-tight seal of the enclosure may be achieved by commercially available seals.

With weathering apparatuses a distinction is made generally between weathering apparatuses with immobile specimens, such as the SUNTEST apparatus of the applicant, and weathering apparatuses having mobile specimens. With weathering apparatuses having immobile specimens surfaces are provided for mounting the specimens on an inner wall of the weathering chamber which is usually the horizontal bottom plate of the weathering chamber, these specimens mostly being rectangular plates of standard size. Facing the bottom plate, i.e., on a top horizontal inner wall, the UV radiation sources are mounted. With weathering apparatuses having mobile specimens, by contrast, the UV radiation source is arranged as a central rod-shaped radiation source and the specimens are mounted on a frame which can be made to rotate. Here too, the likewise usually plate-type specimens having the surface to be tested are exposed to the radiation source continually during rotation.

The device in accordance with the invention can be put to use in both types of weathering apparatuses. In a weathering apparatus in which the specimens are immobile the bottom wall of the enclosure is formed by the mounting surface, formed generally by a portion of an inner wall of the weathering chamber, whereas in a weathering apparatus in which the specimens are mobile an enclosure is provided which is movable within the weathering chamber, it in particular being made to orbit the UV radiation source. In this arrangement the enclosure can be secured to a frame capable of being rotated within the weathering chamber, the top wall of the enclosure comprising the UV radiation filter always facing the UV radiation source.

In weathering apparatuses having immobile specimens, such as the SUNTEST apparatus of the applicant, it is provided for, as a rule, that air is circulated within the weathering chamber such that the air streams over the specimens substantially in a laminar flow in thus ensuring a constant ambient temperature in the direct vicinity of the specimen. This is achievable with a device in accordance with the invention by the two facing sidewalls of the enclosure being formed with ports for passage of a gaseous medium. Preferably, in this case, feeder lines, such as flexible conduits or the like, are directly connected to the ports, so that the ports too, are sealed off to prevent the ingress of stray light into the interior of the enclosure.

In the simplest case, the gaseous medium can be air. But, any other gaseous medium can be used, with which, for example, instead of, or in addition to cooling also a scavenging function is achievable. For example, nitrogen may be employed as the gaseous medium. If, e.g., the enclosure is scavenged with practically pure nitrogen, the oxidation of a specimen such as for example an exposed polymer can be reduced or suppressed, resulting in only the oxygen chemically or physically bound in the specimen becoming effective so that the atmospheric oxygen in the air can be separated and checked as an influencing factor. For such scavenging and, where necessary, also for checking as described above, use can also be made of oxygen gas, particularly pure oxygen gas. Other gaseous media could be put to use and their oxidative and reductive effect tested.

It may furthermore be provided for that a cooling means for cooling the specimen is sited at the side of the bottom wall of the enclosure facing away from the UV radiation filter or in the bottom wall itself. The cooling means may also involve water cooling or a cooling assembly.

In a weathering apparatus in which the specimens are immobile, such as the SUNTEST apparatus, a plurality of mounting surfaces, called stages, for mounting a corresponding plurality of specimens are usually provided. In this case it may be provided for that a corresponding number of enclosures is provided, each enclosing a specimen.

As an alternative, it may also be provided for that several specimens are arranged within an enclosure, meaning that a plurality of specimens is sited on the bottom wall of the enclosure, enclosed by a single common enclosure. Both variants as described are feasible in both weathering apparatuses in which the specimens are immobile and in which the specimens are mobile.

The UV radiation filter is, for example, an edge filter, the edge of which is formed by a transition located within a certain wavelength range between an absorbing and a transmitting condition of the UV radiation filter. As already explained at the outset, in applications such as determining the sun protection factor or the like, edge filters are of interest in which the wavelength 320 nm is contained in the wavelength range of the transition. The transmission of a commercially available WG320 filter amounts to 50% for a wavelength of 320 nm. The UV radiation filter used in the present invention may thus be composed as a WG320 filter, it being necessary to adapt the filter in shape and size so that it fits in an enclosure. It is, however, just as possible that other edge filters or interference filters having suitable edges (transition between an absorbing and a transmitting condition) can be put to use for testing aging effects.

BRIEF DESCRIPTION OF THE DRAWINGS

The invention will now be detailed by way of example aspects with reference to the drawings in which:

FIG. 2 is an example aspect of a light or weathering testing device in accordance with the invention.

DETAILED DESCRIPTION OF THE PRESENT EMBODIMENTS

Figure 1:
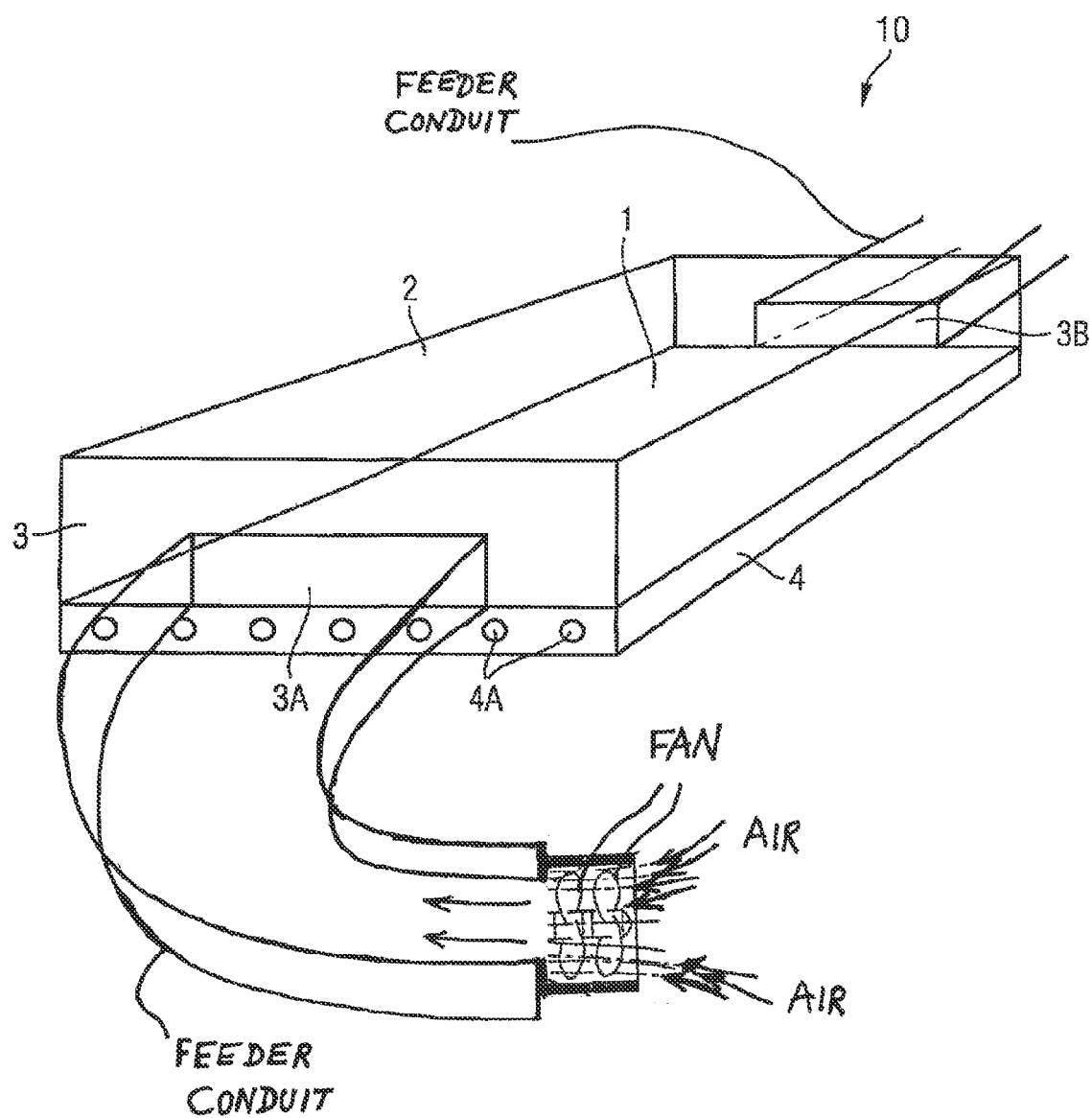
FIG. 1 is an example aspect of an enclosure in accordance with the invention for a light or weathering testing device.

Referring now to FIG. 1 there is illustrated in perspective an enclosure in accordance with the invention for a device for light or weathering testing specimens. The enclosure 10 comprises a bottom wall 1 on which the specimens to be tested can be suitable arranged. For this purpose suitably shaped stages to which the specimens can be secured can be arranged on the bottom wall 1. As is usual for weathering tests, the specimens may be standard size rectangular disks provided with a coating to be tested.

Sited facing the bottom plate is a UV radiation filter 2 constituting the top plate of the enclosure. As described above this UV radiation filter may be a WG320 filter. In the example aspect as shown, the top of the enclosure 10 is entirely taken up by the UV radiation filter. But it may also be provided for that the UV radiation filter is merely provided as a window in an otherwise light-tight top wall. The enclosure 10 is intended to be sited within a device in accordance with the invention so that the UV radiation filter is located between the bottom plate and the UV radiation source arranged in the chamber of the device so that the radiation emitted by the UV radiation source can directly attain the specimens mounted on the bottom plate only by passing through the UV radiation filter 2.

The bottom plate and UV radiation filter 2 are rectangular in shape, as evident from the example aspect. The enclosure 10 comprises furthermore four sidewalls 3 by which the UV radiation filter 2 is connected to the bottom plate 1. The sidewalls 3 themselves and the transition or seam locations between the sidewalls 3 and the bottom plate 1, on the one hand, and the UV radiation filter 2, on the other, are preferably closed off light-tight as is achievable by commercially available seals. This makes it possible that only light filtered by the UV radiation filter attains the specimens. As described above, the xenon radiator also emits light having wavelengths of below 300 nm which can be filtered by the UV radiation filter 2. The light-tight configuration of the enclosure ensures that no stray light whatsoever can gain access to the specimens from the xenon radiator.

The enclosure 10 comprises furthermore two facing sidewalls 3 in which ports 3A and 3B for porting air are formed. Since the specimens are heated up by the irradiation it is usual in weathering apparatuses to stream the specimens with air to cool them down in ensuring an even temperature. The port 3A may be, for example, an inlet port and 3B an outlet port, it being of advantage when light-tight connectors are directly fitted to the ports 3A and 3B for feeder conduits such as flexible air lines or the like, so that no stray light can gain access from the xenon radiator to the ports 3A and 3B and enter the interior of the enclosure 10.

The enclosure 10 comprises in addition a cooling means 4 located beneath the bottom wall, comprising for example drilled conduits 4A extending parallel to each other longitudinally and transversely in the enclosure 10 and through which, for example, cooling water can be directed.

Figure 2:
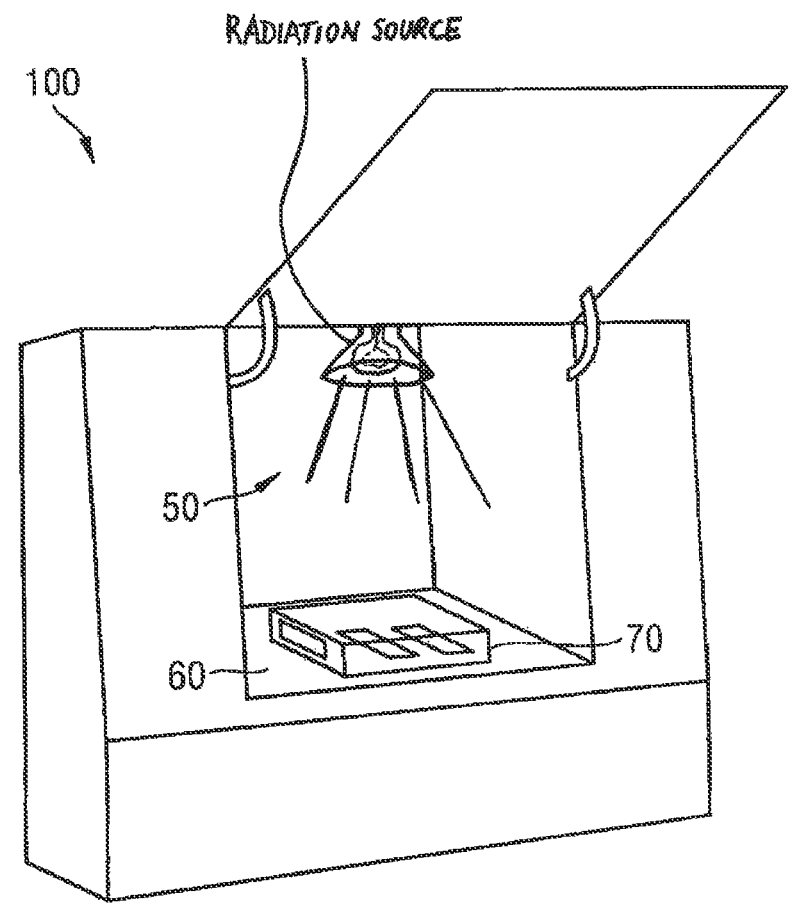
Figure 2A:
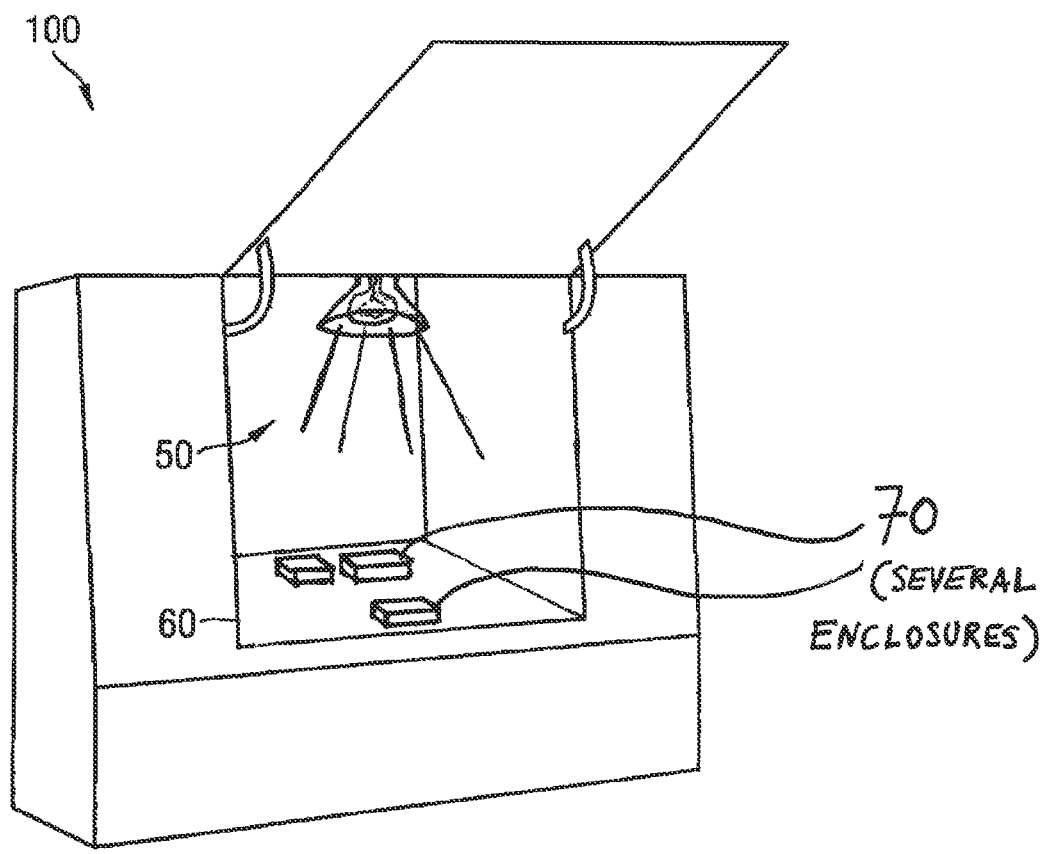
FIG. 2a is another example aspect of a light or weathering testing device in accordance with the invention.
Figure 2B:
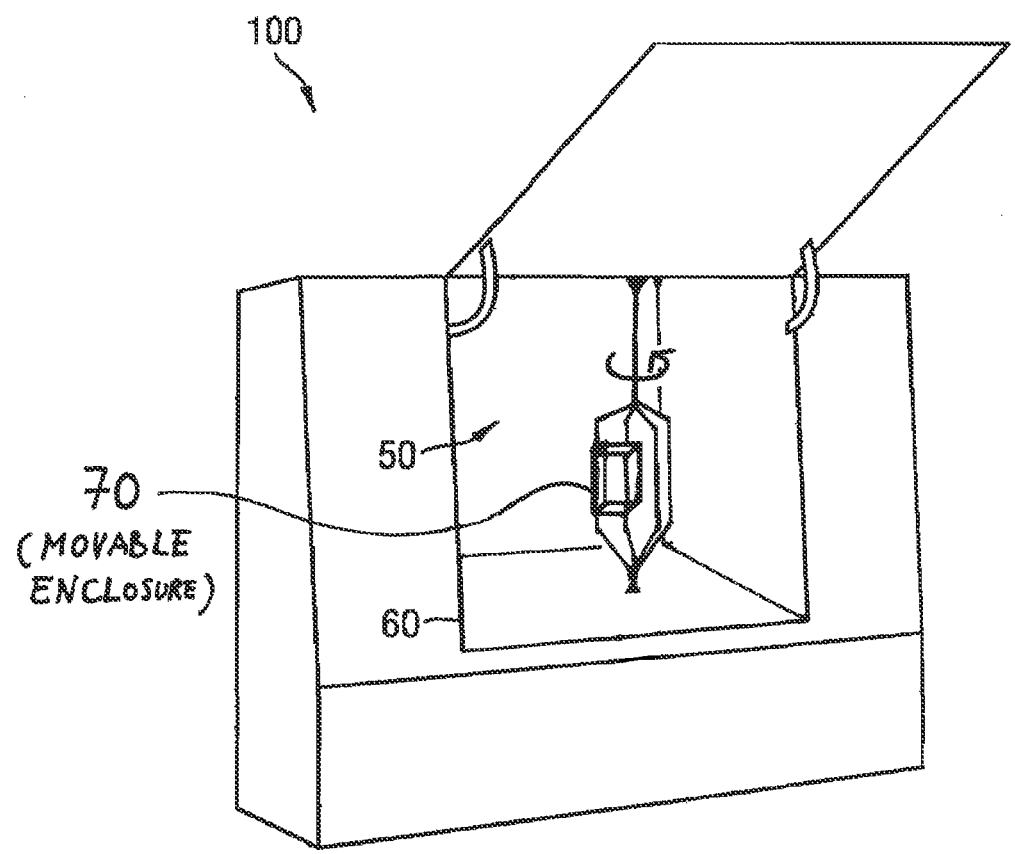
FIG. 2b is another example aspect of a light or weathering testing device in accordance with the invention

Referring now to FIG. 2 there is illustrated an embodiment for a light or weathering testing device in accordance with the invention in a view in perspective showing the specimens. The device 100 in this example aspect involves a weathering apparatus with immobile specimens such as the SUNTEST apparatus of the applicant. The device 100 comprises a weathering chamber 50 which can be hermetically sealed for weathering testing. Fitted to the top wall of the weathering chamber 50 is a plurality of xenon radiators. Sited on a bottom plate 60 are the stages mounting the specimens. Arranged on the bottom plate 60 is an enclosure 70 in which two specimens can be staged. The bottom plate of the enclosure 70 is thus formed by a portion of the bottom plate 60 of the weathering chamber 50. The ports in the facing side surfaces of the enclosure 70 can be connected to flexible air lines (not shown) connected to a fan in the device 100 outside of the weathering chamber 50.

As an alternative it may also be provided for that several enclosures are arranged on the bottom plate 60 each sized roughly the same as a specimen stage so that just one specimen can be accommodated in each enclosure.

What is claimed is:

1. A light or weathering device for testing a specimen, comprising:
    a weathering chamber which can be hermetically sealed, the chamber comprising a top wall and a bottom wall, wherein the bottom wall is configured so as to dispose thereon a plurality of rectangular shaped specimen;
    a UV radiation source mounted on the top wall;
    an enclosure arranged stationary on the bottom wall, the enclosure comprising an enclosure wall enclosing the plurality of specimen, the enclosure wall comprising an upper wall comprising a UV radiation filter, the UV radiation filter being disposed in the light path between the UV radiation source and the plurality of specimen;
    a first cooling means comprising a fan disposed outside of the weathering chamber and flexible feeder lines connected with the fan. wherein the enclosure further comprises two facing side walls, wherein in each one of the facing side walls a port is formed for porting air, namely an input port and an output port, and wherein the flexible feeder lines are connected between the fan and the ports and the fan is configured to suck atmospheric air from outside of the weathering chamber to the flexible feeder lines and from the flexible feeder lines to the input port, wherein the first cooling means is further configured to supply other gaseous media than air to the input port, and the ports comprise rectangular areas of equal size extending over more than half of the lateral width of the sidewalls, respectively, whereas the ports directly face each other so that air can flow unobstructed from the input port to the output port; and
    a second cooling means comprising a water supply and a plurality of conduits connected with the water supply, wherein the conduits are disposed in the bottom wall of the weathering chamber and are formed as throughholes drilled into the material of the bottom wall and each one of the through-holes comprises a circular cross section, wherein the through-holes extend parallel to each other in a direction from below one side wall of the enclosure to below the other side wall of the enclosure.
2. The device according to claim 1, wherein the UV radiation filter is comprised of a WG320 filter.
3. The device according to claim 1, wherein the UV radiation filter is comprised of an interference filter.
4. A method of testing a specimen, the method comprising providing a light or weathering device according to claim 1;

disposing a plurality of specimen in the enclosure on the bottom wall of the weathering chamber;

determining an influencing factor of atmospheric oxygen on the weathering of the specimen by conducting testing in the presence of atmospheric air in the enclosure, and conducting testing in the absence of atmospheric air in the enclosure after scavenging the enclosure with pure nitrogen in order to reduce or suppress an oxidation of the specimen.

5. A method of testing a specimen, the method comprising providing a light or weathering device according to claim 1;

disposing a plurality of specimen in the enclosure on the bottom wall of the weathering chamber;

determining an oxidative or reductive effect of other gaseous media than oxygen or nitrogen on the weathering of the specimen by conducting testing the presence of these other gaseous media in the enclosure.

\* \* \* \* \*